US005692615A

United States Patent [19]
Fischer

[11] Patent Number: 5,692,615
[45] Date of Patent: Dec. 2, 1997

[54] SURGICAL SPONGE MONITOR SYSTEM

[76] Inventor: Michael Fischer, 2030 Arbor La., Northfield, Ill. 60093

[21] Appl. No.: 451,417

[22] Filed: May 26, 1995

Related U.S. Application Data

[63] Continuation-in-part of Ser. No. 179,100, Jan. 10, 1994, abandoned.

[51] Int. Cl.$^6$ .................................................. A47F 7/00
[52] U.S. Cl. ............................ 206/440; 206/486; 211/10; 211/89; 211/70.1
[58] Field of Search ................................ 206/361, 362, 206/440, 486, 488, 489; 211/10, 89, 70.1, 73

[56] References Cited

U.S. PATENT DOCUMENTS 5,072,904 12/1991 Taylor ................................ 211/89

FOREIGN PATENT DOCUMENTS 263812 7/1964 Australia .

*Primary Examiner*—Jacob K. Ackun
*Attorney, Agent, or Firm*—Walter C. Ramm

[57] ABSTRACT

A system for monitoring utilization of surgical sponges with reference to a surgical procedure. The system features a monitor board with a tally panel. The tally panel is generally planar, has reverse and obverse surfaces, and defines a substantial number of trans-panel deposit sites. Each site has small portions adapted suitably to deform in response to application of modest force. When the panel is in in-service orientation, and as the small portions of one site become deformed, the site is adapted to receive and retain a used sponge in trans-panel deposit. Each deposited sponge in part protrudes from the obverse surface and, against the background thereof, is visually accessible and displayed, for tallying. Stands for the monitor board as well as erectile and foldable-as-erected versions of the board and disposal containers for the a board (with a complement of used sponges) are also disclosed.

16 Claims, 6 Drawing Sheets

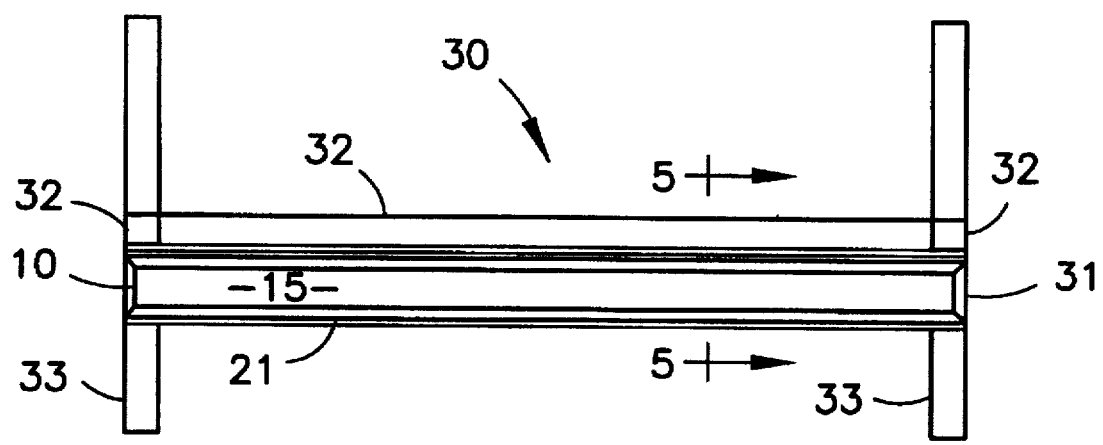
FIG. 4
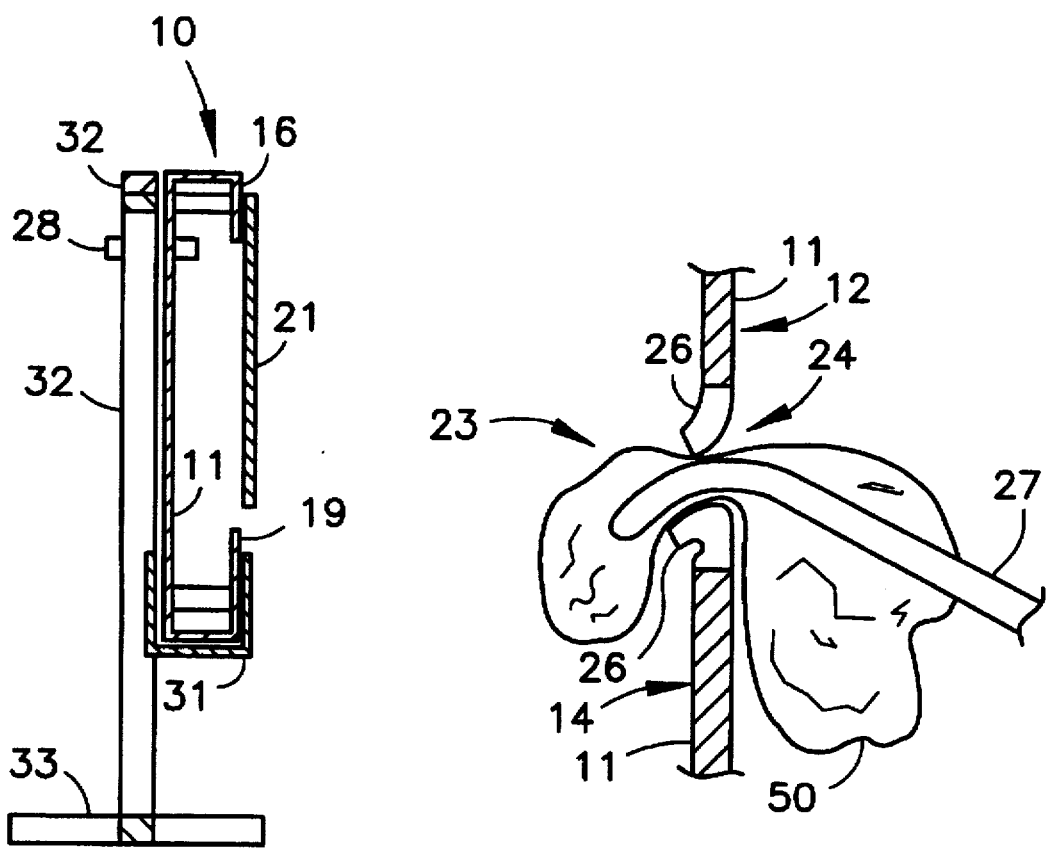
FIG. 5
FIG. 6

SURGICAL SPONGE MONITOR SYSTEM

This is a continuation-in-part of application Ser. No. 08/179,100 filed on Jan. 10, 1994 and now abandoned.

TECHNICAL FIELD

This invention relates to the technical field of special receptacles and similar articles for surgery and, in particular, to articles which receive and retain used surgical sponges for counting and thereby aid in monitoring utilization of sponges in a surgical procedure.

BACKGROUND OF THE INVENTION

While new surgical techniques are tending to reduce blood loss by the patient during a surgical procedure, surgical sponges to stem bleeding and absorb blood remain articles of high importance. A recent survey at a large hospital in North America indicates, apart from procedures inherently likely to involve heavy blood loss, a typical surgical procedure requires more than sixty sponges of 4×4 inch or larger size. Monitoring of sponges during and before completion of a procedure, to account for all sponges issued, and with careful tally of those actually used, likewise continues to be a critical concern and familiar exercise of the surgical team.

Various receptacles and similar products for or to aid tally of used sponges have been proposed, including pouches, pockets and notched parts to receive sponges—see, for example, U.S. Pat. Nos. 4,190,153, to C. E. Olsen, issued Feb. 26, 1980; 4,312,447, to R. M. McWilliams, issued Jan. 26, 1982; and 4,429,789, to P. B. Puckett, Jr., issued Feb. 7, 1984—and some such products are in service. However, unaided manual counting of used sponges is a common routine which, as conducted by a non-sterile nurse and/or other operating room personnel, includes the exemplary steps of collecting used sponges at a space or surface of convenience in the operating room, optional sorting by size, aggregating the sponges in batches of ten (and a final batch of less than ten if such is the case), counting the batches to reckon or check the number of sponges actually used, and placing them into bags for disposal.

This manner of manual routine has disadvantages. Without means to aid the counting or monitoring, the work is slowed and there is increased likelihood of error, uncertainty and avoidable repetition. Some operating room personnel may find collection of used sponges in an open space objectionable because of evaporation effects from blood or other liquid on the sponges.

SUMMARY OF THE INVENTION

In this summary and specification, "sponge" means a surgical gauze sponge or absorbent pad of typical size but not smaller than 4×4 inches. Other typical sponge sizes are (in inches) 4×18, 12×12, and 18×18.

In summary, this invention provides a simple and inexpensive system for or in aid of monitoring of sponges. Objects of the invention, apart from its simple and inexpensive aspects, include products and system components to obviate the noted disadvantages of unaided manual counting and otherwise to assist surgeons and other operating room personnel. For these objects, the system is based on a monitor board with a tally panel providing deposit sites for trans-panel placement or deposit of all used sponges. The system provides a stand to carry the board and may include a disposal container for a board with used sponges in the sites.

The monitor board, on the stand, has upright stance. The tally panel is thin and has first and second surfaces. The board is to be in the operating room in generally vertical orientation and with the first surface manually accessible and the second surface visually accessible. Panel material is normally rigid to maintain in-service orientation and also is characterized in that, in response to modest force applied at a deposit site, small portions of the panel yield to exhibit wanted local deformation in the immediate area of the site.

Each deposit site is arranged to provide trans-panel insertion and deposit of a sponge. A site defines slits in the panel in one of several arrangements—for example, with an aperture in the panel from which the slits extend, or as intersecting slits—and, having regard for panel material, the slits adapt small portions of the panel intermediate or adjacent the slits to be subject to local deformation.

Accordingly, forceps or other suitable hand-held implement, with a working end and a sponge releasibly carried near the end, may be urged against the small portions at a deposit site—proximate the aperture or intersection of slits—locally to deform those portions. Where the site has an aperture, the implement's working end should be slightly larger than the aperture. The action forms a trans-panel opening for implement and sponge to be placed well into and through the panel. Resulting deformation involves effects such as permanent splaying or resilient deflection of the small portions and, in any case, adapts those portions securely to retain the sponge at the site when the sponge is released from the implement and the implement is withdrawn. The panel may thus receive and retain a used sponge in trans-panel deposit at each site, that is, with much of the sponge yet on the first-surface side and with a substantial part protruding and observable on the second surface for tally or enumeration.

The monitor board may advantageously comprise an erectile and subsequently contractible blank. The blanks may be stocked together in flat and compact pre-erected status with each blank, as needed, readily erected and deployed, and then, with a complement of used sponges, disposed of.

To reduce diffusion of objectionable evaporation effects from used sponges, the monitor board may have a transparent dock-type curtain fronting first surface and through which the sponge-carrying implement is readily directed toward an available site.

A photograph of a complement of used sponges, as displayed on the obserse surface, made prior to preparation of the monitor board and the complement for disposal, may serve as a "hard" record of sponge enumeration.

BRIEF DESCRIPTION OF THE DRAWINGS

In the drawings:

FIG. 4 is a plan view of the monitor board of FIG. 1 in the stand of FIG. 2. The curtain fully fronts the first surface.

FIG. 5 is a sectional side elevation view of the stand and monitor board along line 5—5 of FIG. 4.

FIG. 6 is sectional sketch at the aperture and vertical slits of a deposit site of the tally panel and to illustrate deposit of a used sponge at the site.

REFERENCE NUMERALS AND CHARACTERS

Figure 1:
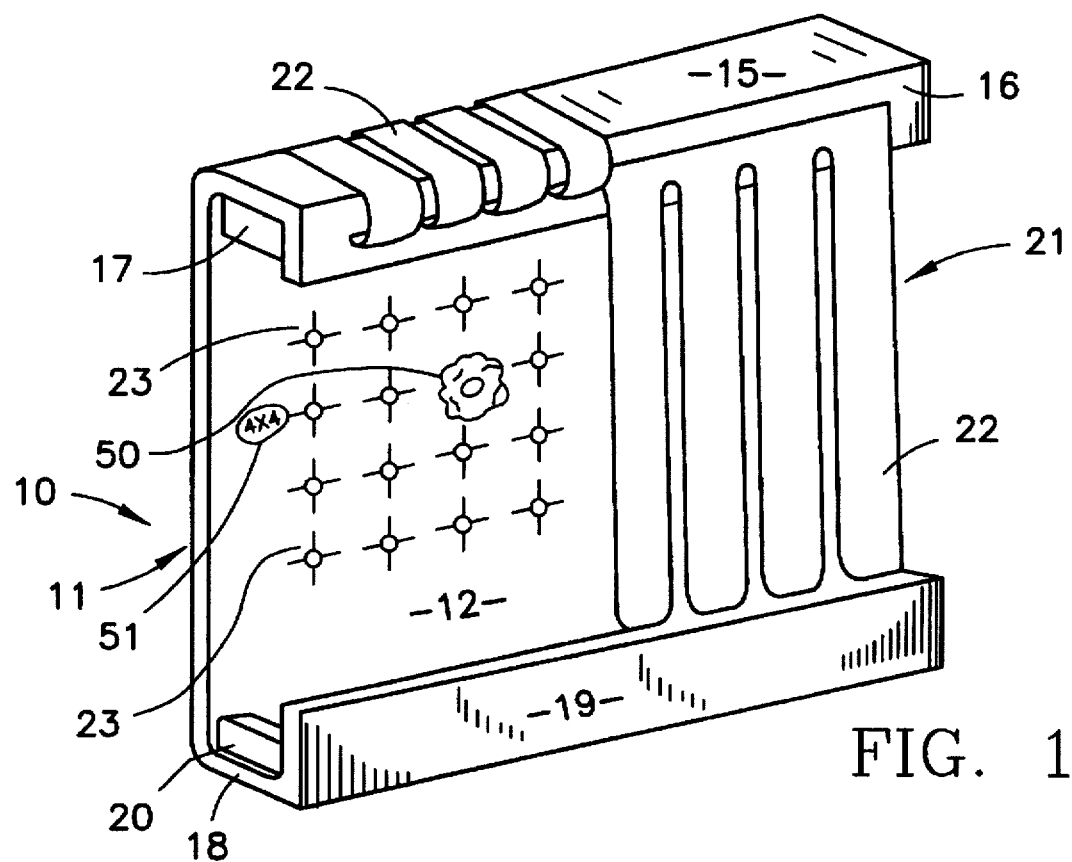
FIG. 1 is a perspective view of a monitor board of this invention and toward the first or reverse surface of the board's tally panel. The board has a curtain comprising transparent flexile elements for the first surface, and some curtain elements are flipped over to the board's other side.

In the drawings and this specification:

Numeral 10 is an exemplary monitor board of this invention, and of or with reference to board 10:

11 is the tally panel,
12 is the first or reverse surface of panel 11,
14 is the second or obverse surface of panel 11,
15 is an upper web,
16 is a fascia member,
17 is an upper end piece,
18 is a trough web,
19 is the trough front,
20 is a trough end piece,
21 is a curtain,
22 is each of several streamer-like elements of curtain 21,
23 is each of several placement or deposit sites of panel 11,
24 indicates the aperture of a site 23,
25 indicates the slits of a site 23,
26 is small panel portion intermediate adjacent slits 25,
27 is forceps, and
28 is a spring clip.

Numeral 30 is a stand for a monitor board, and of stand 30:

31 is a shelf or board holder member,
32 is an upper frame portion, and
33 is leg and foot portions.

Numeral 30' is an alternative stand for a monitor board, and of stand 30':

31' is the lower shelf or slide-in element,
32' is an upper frame portion,
33' is leg and foot portions, and
34 is the upper shelf or slide-in element.

Numeral 40 is a blank for an exemplary erectile monitor board construction, and of or with reference to blank 40:

11' is the tally panel part,
12' is the first or reverse surface of part 11',
14' is the second or obverse surface of part 11',
15' is an upper web,
16' is a fascia part,
17' is an upper flap,
18' is a lower web,
19' is a lower front,
20' is a lower flap,
21' is the curtain,
23' is each of several placement or deposit sites,
41 is a straight edge on part 19',
42 is a transverse fold line,
43 is a bottom-to-top fold line,
44 is a cut portion of part 11' defining a flap 20',
45 is a cut portion of part 11' defining a flap 17'
46 indicates an upper slit, and
47 indicates a lower slit, Numeral 50 is a used sponge, and 51 is indicia of sponge size (as to a row of sites 23).

Numeral 60 is a disposal container, such as a bag, for a monitor board in down-folded or contracted status.

Numeral 70 is a blank for an alternative exemplary erectile monitor board construction, and includes a construction formed of the blank.

Of or with reference to construction 70:

11" is the tally panel,
12" is the first or reverse surface of part 11",
14" is the second or obverse surface of part 11".
21" is the curtain,
23" is each of several placement or deposit sites,
71 is the first component or half of panel 11",
72 is a first top web,
73 is a first fascia,
74 is an upper flap extending from fascia 73,
75 is a first lower web,
76 is a first lower front,
77 is a first lower flap extending from front 76,
78 is a first side web,
79 is a first side front,
81 is the second component or half of panel 11",
82 is a second top web,
83 is a second fascia,
84 is an upper flap extending from fascia 83,
85 is a second lower web,
86 is a second lower front,
87 is a second lower flap extending from front 86,
88 is a second side web,
89 is a second side front,
90 is an hinge element intermediate halves 71 and 81,
91 is the first aspect or side of hinge 90,
92 is the second aspect or side of hinge 90,
93 is an inner transverse fold line,
94 is an outer transverse fold line,
95 is a bottom-to-top fold line associated with half 71,
96 is a bottom-to-top fold line associated with half 81,
97 indicates each of a first and a second lower slots,
98 indicates each of a first and a second upper slots,
99 is an interfold element,
S indicates a scored line on the blank, and
C indicates a cut line or portion.

DESCRIPTION OF BEST MODES FOR CARRYING OUT THE INVENTION

The drawings illustrate various aspects of preferred embodiments of and best modes for carrying out this invention. Board 10 in FIGS. 1–2 and 4–5 represents a generalized best mode. In FIG. 1, the board is upright and has an exemplary configuration and in-service orientation. Webs 15 and 18 extend outwardly, respectively, from top and bottom of panel 11. The panel is essentially planar with parallel surfaces of which surface 12 is shown. Fascia member 16 is on the upper web, and front 19 is on the lower web. The webs serve to space the fascia and front 19 from the panel and, as depicted, preferably extend at right angles to the panel. The fascia and front 19 each may be planar, and they may be parallel to the panel and co-planar. Front 19, the lower web and lower part of the panel form a trough-like lower feature or portion of the board—which, hereinafter, is called the "trough"—and the fascia, the upper web and upper part of the panel form an upper portion.

Each piece 17 and 20 is exemplary means operative between panel 11 and, respectively, fascia 16 and front 19 to assure their spaced relationships and to maintain the in-service configuration and stance of board 10. A piece 17 may be near each upper corner and a piece 20 near each lower corner of surface 12 and, respectively relative to the fascia and the front, may be glued, mechanically affixed or otherwise conveniently attached. Other such means to maintain the spaced relationships and illustrated configuration are acceptable.

Panel 11 defines a plurality of sites 23. For purposes of this description, FIG. 1 shows a sponge 50 as in trans-panel deposit one site. Each site has slits 25 and, preferably, aperture 24. Typically, the aperture is circular, and the slits are radial of the aperture. If no aperture is provided, the slits intersect. The aperture and slits are also "trans-panel" because they extend between surfaces 12 and 14. The trough may receive liquid material, if any, which may drip from a sponge at a site. Curtain 21 hangs from fascia 16 to front much of surface 12 when board 10 is upright. The curtain reduces diffusion of evaporation effects from received sponges. The curtain may be of the so-called "dock" type with a number of elements 22, and is, in any case, transparent, thin and separable. Elements 22 are flexile and readily separable. Exemplary curtain material is a polyvinyl chloride sheet of 4 mil thickness cut to size and to form streamers, and adhesively or otherwise conventionally attached to the fascia.

Figure 2:
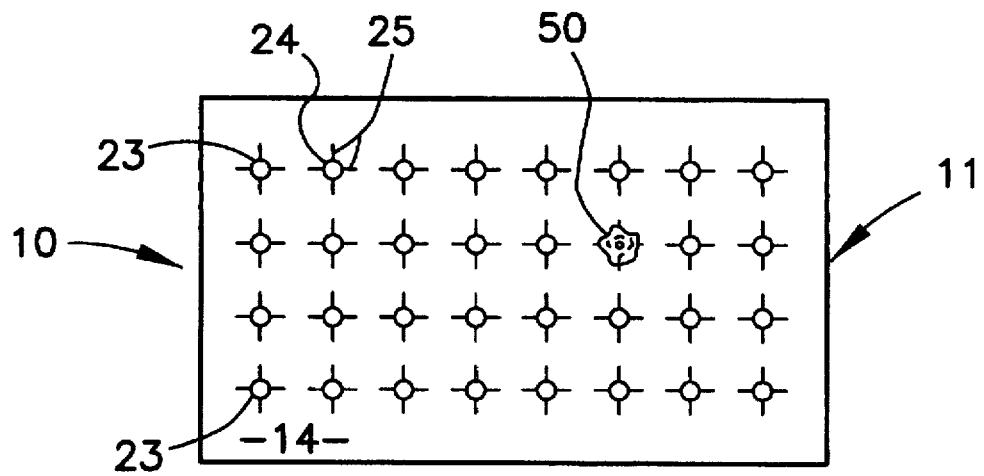
FIG. 2 is an elevation view of the second or obverse surface of the monitor board of FIG. 1.

FIG. 2 depicts the side of board 10 opposite the side appearing in FIG. 1, that is, surface 14 of panel 11 with, again, a part of the sponge 50 of FIG. 1 in trans-panel deposit and protruding from and plainly visually accessible and displayed for tally against the background of the obverse surface. Persons who count or tally used sponges look directly upon the obverse surface.

Figure 3:
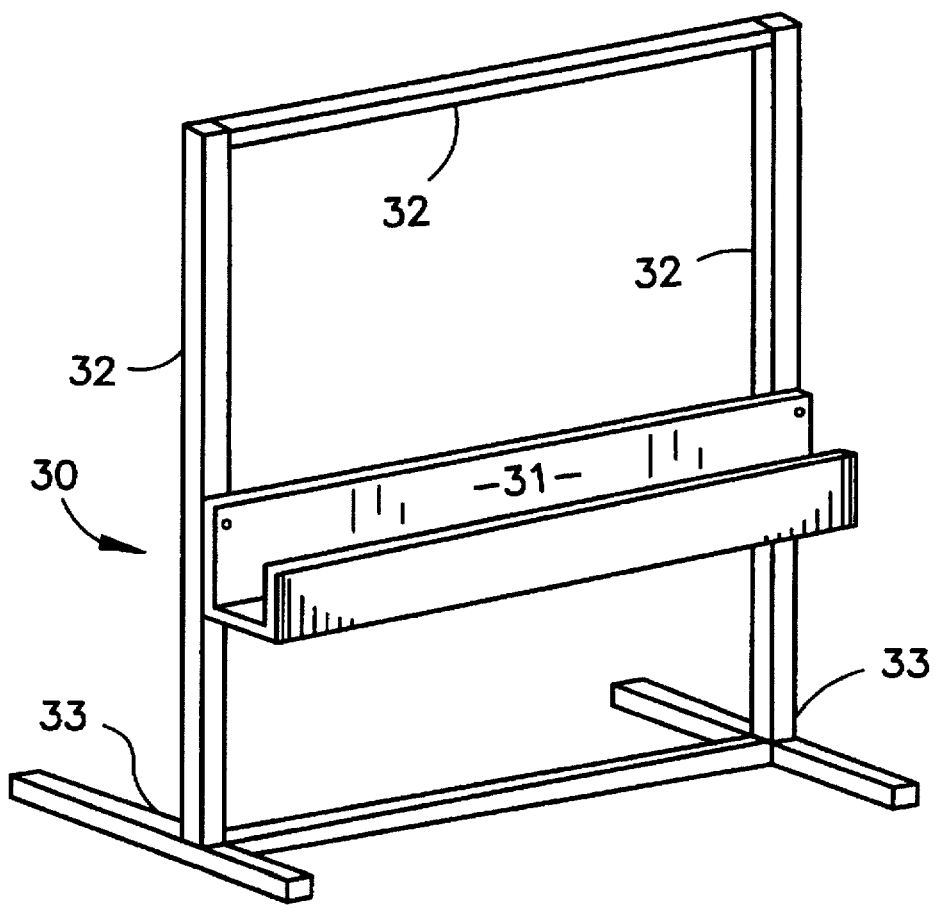
FIG. 3 is a perspective view of a monitor board stand.

FIG. 3 generally illustrates exemplary stand 30 for board 10. The stand has shelf 31, frame 32 and foot-and-legs lower portions 33, and, on a floor or other horizontal surface, is supported on and by portions 33. The frame has generally vertical orientation and, in any case, corresponds with the in-service orientation of the board and panel 11. Shelf 31 may be a so-called "J" shelf whereof the vertical sides may be notably thin. Portions 33 are adapted suitably to support against a moment on the board in the stand as might arise from modest force against the board at a site 23.

FIG. 4 shows board 10 upright on stand 30 and with the trough positioned on and within, and carried on, shelf 31. Panel 11 is in generally vertical in-service orientation. The board is sized so as to be positionable on the stand and in the shelf to take support from frame 32. For example, in FIG. 4, web 15 extends between side members of the frame, so that upper outer edges of surface 14 and the frame may be adjacent and in contact, or very closely approach that relationship. The width of the trough and inner back-to-front dimension of the shelf conform so that, while the trough (with other parts of the board) may be readily mounted or settled into and, likewise, lifted from or demounted from the shelf, as and when the board is on the shelf, the trough fits snuggly in and is kept from back-to-front or other unwanted movement as to the shelf.

Sectional FIG. 5 corresponds with FIG. 4 and shows also clip 28 operative between board 10 and frame 32, and affirmatively holding the board onto the frame with panel 11 in in-service orientation. Means such as the clip are optional but, against a possibility the board may warp, serve supplementally to assure proper orientation of the panel.

FIG. 6 illustrates trans-panel insertion and deposit or placement of a sponge 50 at and in a site 23 by means of forceps 27 in which the sponge is releasibly carried. Each small portion 26 is locally deformable. A person making the deposit works toward surface 12. As and after the person has passed forceps and sponge through separated elements 22 and, as shown, pushed with modest force on the small portions and through aperture 24, those portions locally splay or spread beyond undeformed portions of surface 14 with, perhaps, some surface effect on or fracture of material, and are disposed, contoured and fitted to clutch or engage the sponge. Gauzy sponge material is suited for such clutching or engagement. After the person has ceased to apply force, released the sponge, and withdrawn the forceps, those portions serve then and thereafter to retain the sponge at the site (see also FIG. 2).

Figure 7:
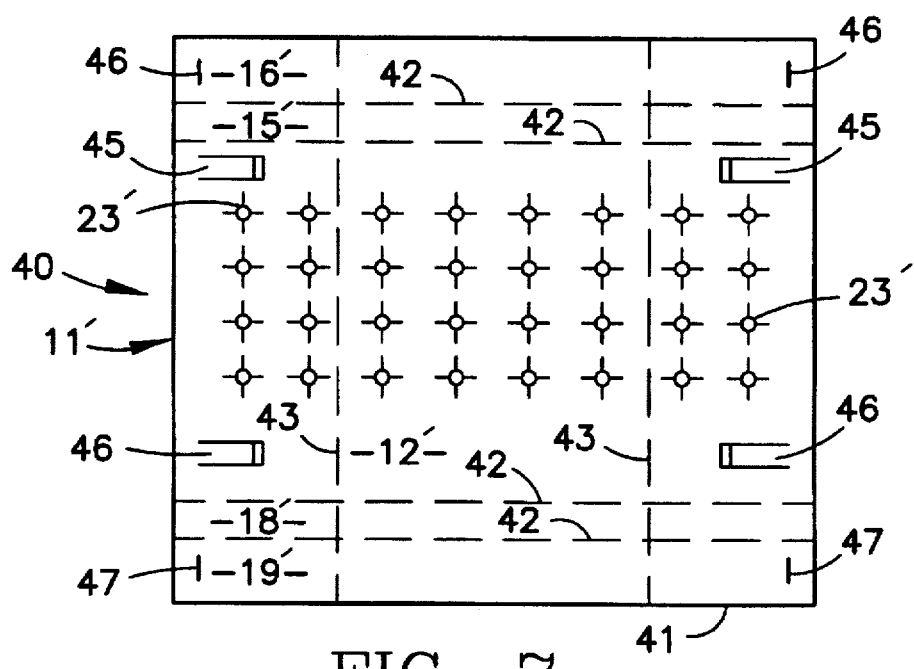
FIG. 7 is a plan view of a blank for an erectile version of the monitor board of this invention. The blank is flat and unfolded.

In FIG. 7, blank 40 is for monitor board construction as a specific preferred embodiment and best mode of this invention whereof the board is erectile and subsequently collapsible. The blank is a flat, unfolded sheet material, and has (for reference) edge 41. Surface 12' is upward, and surface 14' (not shown in FIG. 7) is downward. Panel part 11', webs 15' and 18', fascia part 16', front 19', and sites 23' are functionally and organizationally the same as corresponding parts of board 10 (FIG. 1).

However, rather than ends such as ends 17 and 20, blank 40 has cut portions 45 and 44 to provide, respectively, flaps 17' and flaps 20' as exemplary flap means on the blank to assure proper configuration of the blank, as erected and on a stand 30 or otherwise in use. Flaps 17' and flaps 20' serve to space, respectively, fascia part 16' and front 19' relative to panel part 11'. Specifically, a flap 17' is near each upper corner and a flap 20' is near each lower corner of the panel part, each flap 17' is arranged to fit with its corresponding slit 46 in the fascia part, and each flap 20' is arranged to fit with its corresponding slit 47 in front 19'.

Still referring to FIG. 7, a blank 40 construction includes four transverse fold lines—that is, first, second, third and fourth lines 42—and at least one bottom-to-top fold line 43. Each transverse fold line is parallel to edge 41. First line 42 is between fascia part 16' and web' 15', second line 42 is between web 15' and panel part 11', third line 42 is between the panel part and web 18' and fourth line 42 is between web 18' and front 19'. The transverse fold lines adapt the blank to be folded—with the flaps inserted and retained in their slits—to a configuration which generally resembles board 10. Each line 43 is at a right angle to edge 41 and enables the blank, ultimately, to be folded or closed upon itself. Lines 42 and 43 are scored or, preferably, perforated to facilitate folding and down-folding of the construction and to eliminate unwanted "memory" from the material.

Figure 8:
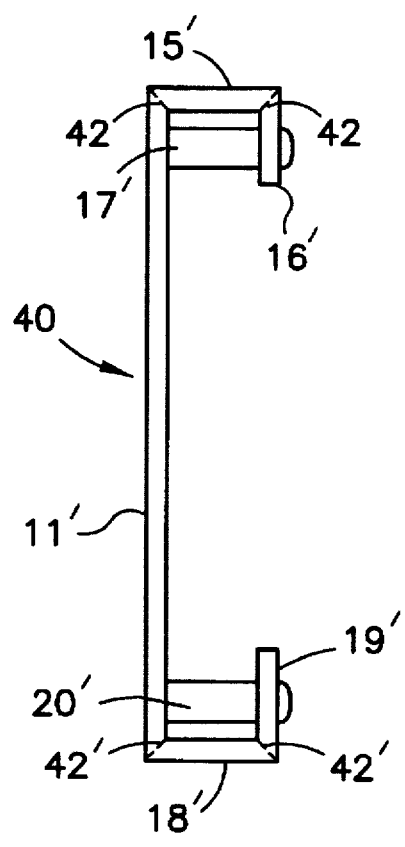
FIG. 8 is a side elevation of the blank of FIG. 7 as erected to comprise a said monitor board.

Referring to FIG. 8, the blank 40 construction is erected and assembled to comprise a monitor board of this invention as in in-service status. Web 15' and fascia part 16' comprise a now-formed upper part of the blank. Flaps 17' and 20' fold out from panel part 11' and are respectively fitted with and in slits 46 and 47. The blank and its now-formed trough part may be carried on stand 30 with the panel part in generally vertical orientation and to receive and retain sponges in the same trans-panel manner as described with reference to board 10 and panel 11. The construction has yet to receive a curtain.

Figure 9:
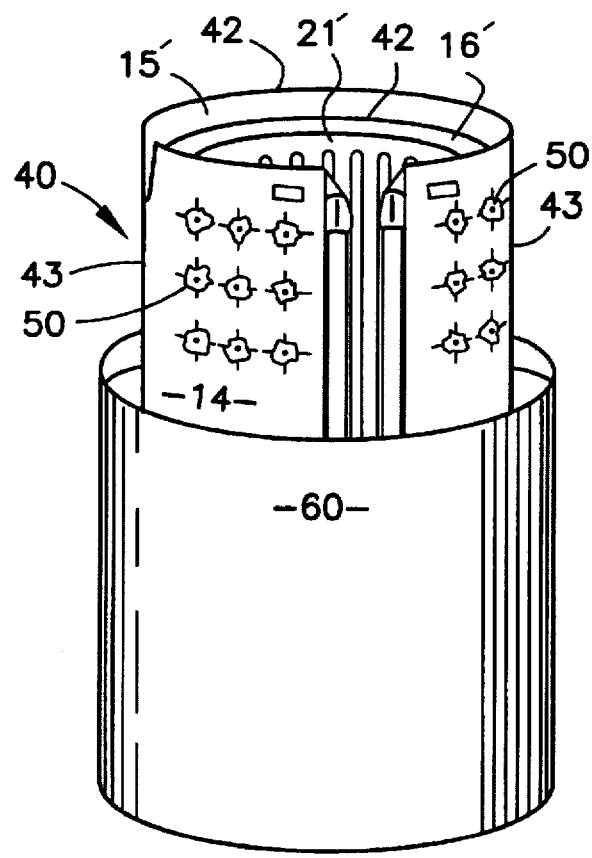
FIG. 9 is a sketch of the blank of FIG. 8 as disassembled, ready for disposal, and partially in a disposal container.

In FIG. 9 blank 40 is de-assembled and collapsed from the erect status of FIG. 8 and ready, with its complement of used sponges 50, for disposal and, indeed, is already partially into bag 60. Flaps 17' and 20' are out of their slits so the blank has lost monitor board configuration. Web 15' is down-folded along second line 42. Fascia part 16' is down-folded along first line 42 and over the upper course of used sponges, and curtain 21' is in disarray. Web 18' and front 19' are down-folded along third and fourth lines 42. The trough has disappeared. As shown and relative to the construction of FIG. 7, the blank is folded cabinet-like upon itself along lines 43 to enfold surface 12' and become somewhat amorphous and ready to be placed into the bag. Throughout de-assembly and down-folding, of course, operating room personnel wear gloves and comply with mandates and precautions governing handling and disposal of blood-containing materials.

Figure 10:
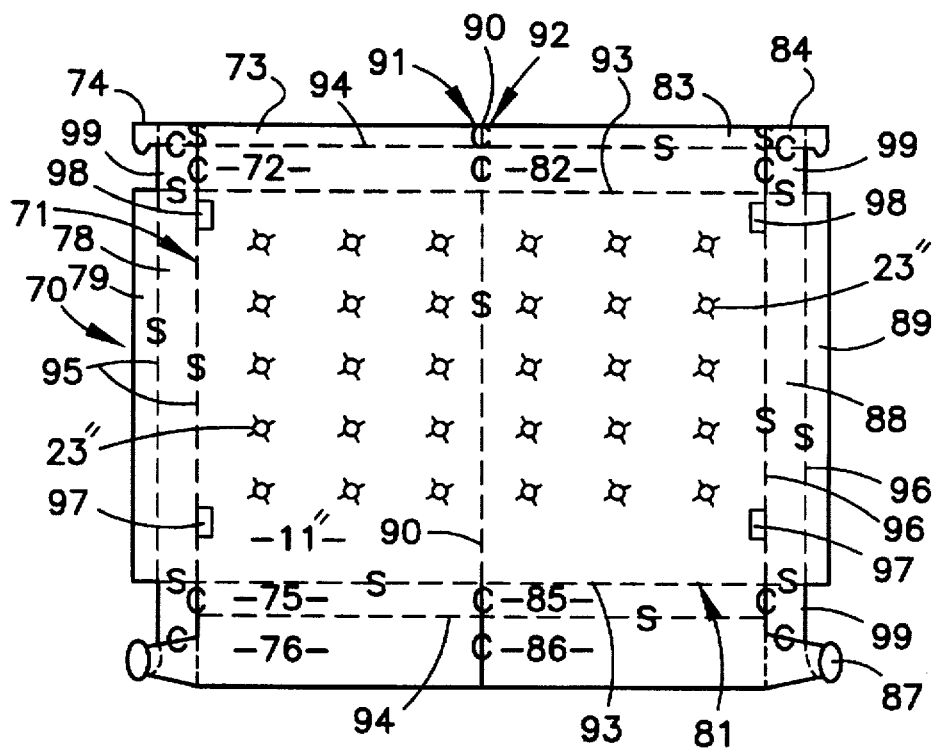
FIG. 10 is a plan view of the blank for an alternative erectile version of the monitor board of this invention. The blank is flat and unfolded.

Referring to FIG. 10, blank 70 represents an alternate preferred construction for and embodiment of, and best mode of, an erectile monitor board of this invention. This exemplary blank is flat, unitary sheet material, and organized with halves 71 and 81 as elements of panel part 11" and hinge 90 between the halves. The exemplary hinge is embodied as a fold line within a narrow portion of the sheet material, has aspects 91 and 92 on respective sides of the line, and renders the panel part foldable along the line. Each half defines a plurality of sites 23", is planar and rectangular, and has inner, outer, upper and lower edge-portions. The inner edge-portion of half 71 is along aspect 91. The inner edge-portion of half 81 in along aspect 92. Again, on the blank of FIG. 10—preferably and in the drawing notation of the blank-fabricating art—S indicates a scored line and C indicates a cut portion or line.

Blank 70 has parts for channels including webs 72, 75 and 78 at respective upper, lower and outer edge-portions of half 71; fascia 73 on web 72; front 76 on web 75; front 79 on web 78; webs 82, 85 and 88 at respective upper, lower and outer edge-portions of half 81; fascia 83 on web 82; front 86 on web 85; and, front 89 on web 88. These parts are generally rectangular and defined by transverse lines 93 and 94 and bottom-to-top lines 95 and 96.

Blank 70 also has flap 74 on fascia 73, flap 77 on front 76, flap 84 on fascia 83, flap 87 on front 86, first slots 97 and 98 in half 71, and second slots 97 and 98 in half 81. Each flap has an end-portion with an eared tab, and in the unfolded blank of FIG. 10, generally extends normally of hinge 90.

Blank 70 is arranged for easy manual assembly at any time after the blank has been fabricated, and so that, as the blank is folded at 90° angles along lines 93-96, and with allowance for thickness of the sheet material, the channels take shape, and the flaps may be engaged with panel 11".

Elements 99 are optional, but as they are provided, and each is reverse-folded toward the side web from which it extends, they aid formation of the side channels. Specifically, the flap-panel engagements are made with eared tabs of respective flaps in specific slots—flap 74 in first slot 98, flap 77 in first slot 97, flap 84 in second slot 98, and flap 87 in second slot 97. These flaps-slots means obviate need for tools or materials such as glue or staples, and serve to maintain erect status of the assembled board.

Figure 11:
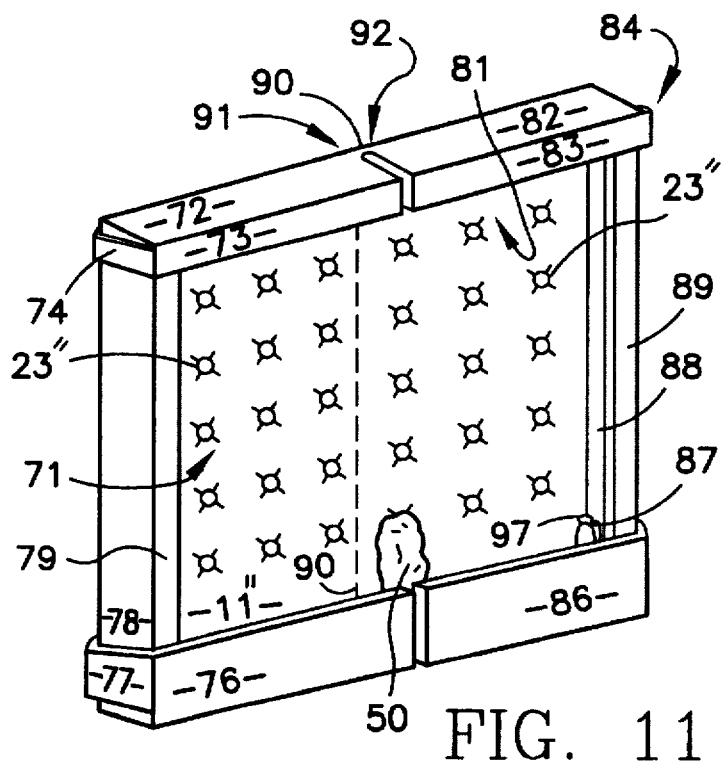
FIG. 11 is a perspective view of the blank of FIG. 10, as and when erected to comprise a monitor board. The board is in deployed configuration. The view is toward the first or reverse surface of the tally panel of the board.

FIG. 11 illustrates construction 70 as a monitor board of this invention in assembled status and in deployed or open configuration. Concerning assembled status, the board has channels—on half 71, a first upper channel with web 72/fascia 73, a first lower channel or trough with web 75/front 76, and a first side channel with web 78/front 79; and, on half 81, a second upper channel with web 82/fascia 83, a second lower channel or trough with web 85/front 86, and a second side channel with web 88/front 89. Flaps 74 and 77 pass around the first side channel. Flaps 84 and 87 pass around the second side channel. The tab of flap 87, in second slot 97, appears as engaged with half 81, and the other flaps are their slots and in like manner engaged. Webs 75 and 85 are coplanar, and the troughs afford an exemplary base. The side channels contribute strength, rigidity and something of "pizza-box" character to board 70, and in these respects represent relative advantage over construction such as board 40. A curtain is yet to be provided. Concerning deployed configuration, board 70 in FIG. 11 is ready to receive a complement of used sponges for tally. Hinge 90 is unfolded or unturned. Halves 71 and 81 are generally coplanar, form panel 11" and the panel's obverse and reverse surfaces, and provide an array of sites 23". The first and second troughs form a composite trough, the first and second upper channels form a composite upper channel, the side channels are opposed, and these trough and channel features, together, are peripheral of the panel and extend outwardly of the reverse surface. Webs 78 and 88 are parallel, and the board presents a rectangular profile. Fascia 73 and and front 76 are coplanar and define a first frontal plane as to half 71, fascia 83 and front 86 are coplanar and define a second frontal plane as to half 81, and as all said fascia and fronts are, as shown, generally coplanar, they define a composite frontal plane. The side channels are within such composite frontal plane.

FIG. 11 shows a sponge 50 in trans-panel insertion at a site 23", as described (see FIG. 6) of the lowest row of the sites array. The larger part of this sponge hangs into the composite trough. As additional sponges are received in unoccupied sites, similar portions thereof will likewise hang toward or into the trough, and the trough may receive fluid material from them.

Figure 12:
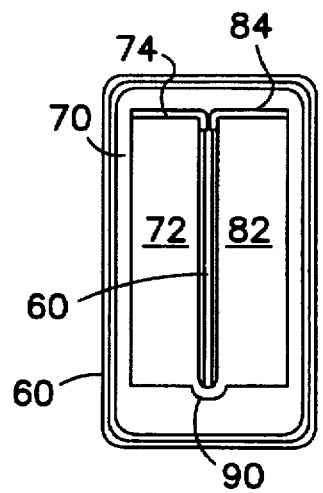
FIG. 12 is a plan view of the monitor board of FIG. 11. The board is in compact configuration and within a shipping/ disposal container.

Referring to FIG. 12, board 70 is in assembled status but as folded or shifted—around flexed hinge 90—to compact or down-folded configuration. The hinge enables such shifts to and between each of deployed and compact configurations although not more than, say, two such shifts need be expected during the life of the board. The positions of webs 72 and 82 indicate that halves 71 and 81 are turned from the coplanar relationship of FIG. 11 by an angle of, say, 175°, and, in any case, closely approach parallelism and each other. The fold line of the hinge, as preferably scored, is unlikely to retain "memory", but as the board is at rest on the lower webs—with or without a complement of used sponges—its inertia exceeds any resilience of the hinge, and the halves are unlikely notably to displace. If desired, a string or some other simple, inexpensive and conventional means may be provided to hold the halves together in compact configuration.

As to board 70 in compact configuration with a complement of used sponges in sites 23", the protruding forward parts of the sponges are sandwiched between halves 71 and 81, and the halves may deflect slightly to accommodate those parts. Bulk comprising the remaining parts of the sponges in each half is well within the trough or frontal plane of the half.

FIG. 12 shows board 70 inside of container 60. This exemplary container, which appears as partially turned down and still unclosed, is preferably a transparent, gas permeable "biobag", and contoured to receive and suitably to enclose or encase one board in compact configuration. Compact configuration is highly satisfactory for packing/shipping an already assembled board, prior to use, in such a container, as well as for post-tally disposal of the board with a complement of used sponges and, again, within the same container. Thus, for a circumstance of compact configuration, board and container are a useful assemblage.

Figure 13:
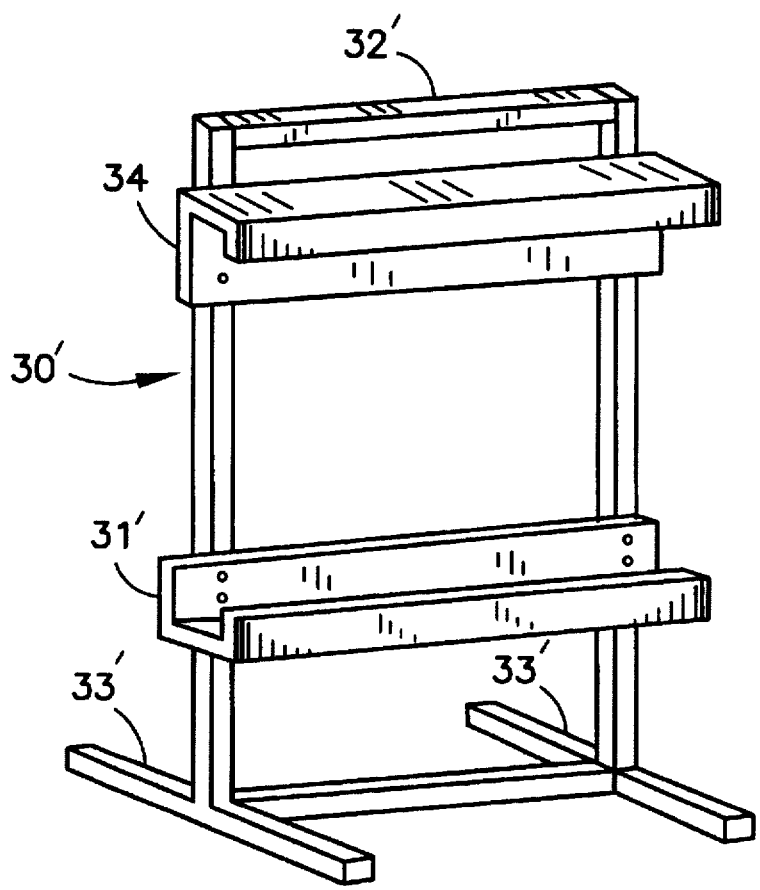
FIG. 13 is a perspective view of a stand for the monitor board of FIG. 11.

FIG. 13 depicts stand 30' as an exemplary two-shelf holder for board 70 in deployed configuration. Stand 30', with frame 32' and legs/feet 33', in some respects resembles stand 30, but it has the two shelves, that is, lower "J" shelf 31', and upper inverted "J" shelf 34 on the frame. The shelves are of equal length, horizontal, parallel and vertically spaced, and define a transverse rectangular channel which generally corresponds with the profile of board 70 in deployed configuration. A board may be mounted by sliding it in, from an end of said channel, and centering it as to the shelves.

Figure 14:
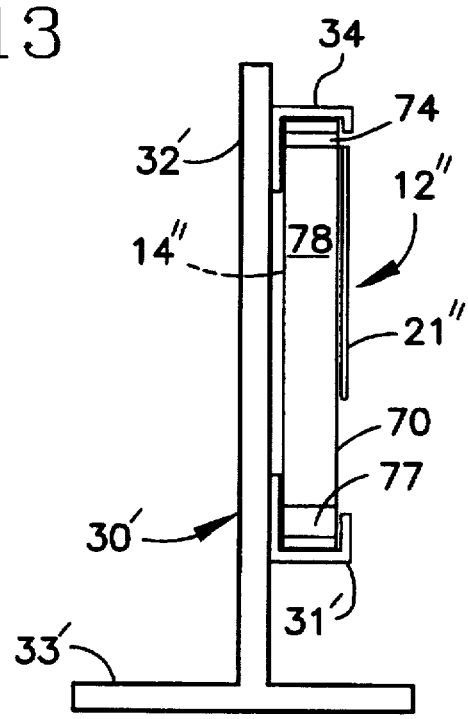
FIG. 14 is a side elevation view of the monitor board of FIG. 11 on the stand of FIG. 13.

FIG. 14 illustrates mounted board 70, in profile, on stand 30'. The fit is close so to retain the board against unwanted displacement but not so tight as to inhibit sliding action between them for mounting the board, and, later, to demount it. Shelves 31' and 34 cooperate to maintain the board in upright stance and in-service orientation, and obviate need, if any, for clip 28 (FIG. 5) or other means, to assure the orientation. Curtain 21", with streamers like elements 22 on both fascia, hangs proximate the frontal plane.

Other forms of two-shelf stand may be provided such as where the upper shelf is conventionally adjustable in front-to-back sense, as by screw means, lightly to grip and to release the upper channel of an emplaced monitor board such as board 40 or board 70. Board 70 may, as well, be carried on a stand 30.

A monitor board, such as board 10, is fabricated of material which is suitably rigid and adapted locally to deform, as described. Heavy cardboard sheet material known as 275 pound "C" board is an exemplary such material. A tally panel, such as panel 11, may have deposit sites, such as sites 23, in an array of horizontal rows and with each site in an aperture with radial slits arrangement. The obverse surface of a tally panel, such as surface 24, may have white clay finish to enhance visibility of protruding and to-be-tallied sponges.

A construction, such as blank 40 or blank 70 is advantageously a single or unitary die-cut piece of said 275 pound "C" board with these additional and exemplary particulars of dimension, capacity and appearance. Blank 40 in flat status is 48 (transverse)×63 (bottom-to-top) inches overall and provides an array of eighty-eight spaced deposit sites in eight horizontal rows. Each site has an aperture with diameter of, say, 0.188 inch and four equally spaced radial slits each with length of, say, 0.875 inch. Each bottom-to-top fold line is 12 inches from the near side edge of the panel. Blank 70 in flat status is 58 (transverse)×45 (bottom-to-top) inches overall, with webs width of, say. 3 inches, and panel 11" provides for an array of as many as eighty-four deposit sites in seven horizontal rows and equally divided between halves 71 and 81. Each site has an aperture with diameter of, say, 0.25 inch and four equally spaced radial slits each with length of, say, 0.75 inch. Each of inner lines 95 and 96 is 24 inches from inches line 90. Again, the obverse surface 14, 14' or 14" has white clay or oyster finish. The side of the blank with reverse surface 12, 12' or 12" may have Michaelman coating. One such blank provides a construction to accommodate a number of sponges somewhat more than the number likely to be used in many surgical procedures, and, as additional sponge capacity may be needed, a second blank may be quickly erected and deployed as a monitor board.

While a blank, such as blank 40 or blank 70, when erected as a monitor board, has a brief in-use life corresponding with the time needed for a surgical procedure, a stand such as stand 30 or stand 30', is more permanent. An exemplary stand may comprise 1-inch square chrome tubing with these dimensions (in inches): width, 48; height, 66, and foot length, 24. Shelf 31, shelf 31' and shelf 34, as the case may be, may be fabricated of plexiglass or other suitable material, and is conventionally attached to frame 32 or frame 32'.

A tally panel, such as panel 11, 11' or 11", may carry indicia 51 as to the size of sponge for particular sites 23. Operating room personnel may mark or apply these indicia to reflect anticipated sponge usage, and these indicia may be, for example, hand-scribed markings or adhesive stickers supplied with the monitor board. Typically, these indicia identify the sites of a particular horizontal row, and, if and as so employed, they should appear as to identified sites both on surface 12 and on surface 14 (see FIGS. 1–2).

Other embodiments of the monitor board and other components of the system are within the spirit and scope of this invention.

What is claimed is:

1. A monitor board, to receive surgical sponges for tally, which comprises a trough including at least one lower web and a lower front on each lower web;

a tally panel
        arranged to extend upwardly in in-service orientation from each lower web, and
        defining an obverse surface, a reverse surface and a plurality of deposit sites;

an upper channel on the panel and including at least one top web and a fascia member on each top web;

a first side channel on the panel and including a first side web and a first side front on the first side web; and, a second side channel on the panel, generally opposed to the first side channel, and including a second side web and a second side front on the second side web;

whereof the trough and each channel extend outwardly from the reverse surface, each deposit site has a portion which is adapted locally to deform in response to modest force applied from the reverse surface and thereby to provide the site for trans-panel insertion of a sponge from the reverse surface and, as to a sponge in trans-panel insertion at the site and when force is no longer applied, there to retain the sponge with a part of the sponge protruding from and displayed against the background of the obverse surface.

2. A system for tally and disposal of surgical sponges comprising a stand including an upwardly extending frame and
a monitor board holder on the frame; and
a monitor board to be carried on the stand and comprising portions adapted to be received in the holder,
a generally planar tally panel
presenting a first surface and a second surface,
arranged for in-service orientation and to take support from the stand when the lower portions are received in the holder, and
defining a plurality of trans-panel deposit sites and deformable portions at each site; and
so that, when the monitor board is carried on the stand, the deformable portions at a site adapt the site for insertion of a sponge from the first surface and to receive and retain the sponge with a portion thereof protruding from the second surface and visually displayed for counting.

3. The system of claim 2 where the monitor board is arranged to be demounted from the stand, has a fascia member on and spaced from the panel when the board is upright on the stand, and has transparent and separable curtain elements for the first surface on the fascia member; and, where system includes a disposal container for the monitor board when the monitor board has been demounted from the stand.

4. In an erectile monitor board construction formed from a blank of normally rigid and locally deformable sheet material
a panel part including
a first surface and a second surface,
first and second transverse fold lines, and
a plurality of deposit sites intermediate the first and second fold lines whereof each site comprises small portions of the panel part which are locally deformable
a trough part with a first web extending from the panel part at the first fold line, a front extending from the first web, a third transverse fold line between the first web and the front; and,
an upper part with a second web extending from the panel at the second fold line, a fascia part extending from the second web, and a fourth transverse fold line between the second web and the fascia part;
so that, when the panel part has in-service orientation, the deformable portions at a site adapt the site for insertion of a sponge from the first surface and to retain an inserted sponge with a portion thereof protruding from the second surface and visually accessible for tallying.

5. Erectile construction according to claim 4 where each of the panel part, webs, front and fascia are substantially planar; the front defines a straight edge; the transverse fold lines are parallel to the straight edge; each site defines a trans-panel aperture and trans-panel slits extending from the aperture; the deformable portions of each site are intermediate the slits of the site; the blank is sheet material comprising 275 pound "C" board and includes at least one bottom-to-top fold line at a right angle to the straight edge; each fold line is perforate; and, the construction includes flap means operative as to the panel part and the blank for spacing the front from the panel part and for spacing the fascia part from the panel part when the blank is in erected status.

6. A surgical sponge monitor board, to receive used surgical sponges for tally and subsequent disposal, which comprises
first and second base parts,
a first planar component on the first base part, and
a second planar component
on the second base part and
extending from the first planar component,
whereof each planar component defines a plurality of sites, the planar components are foldable as to each other and enable the board to be shifted to and between
(a) open configuration in which the planar components extend in upright stance on their respective bases, are coplanar and form a tally panel with a obverse surface and a reverse surface, and
(b) down-folded configuration in which the planar components are close to each other and approach parallelism, and the bases are outward; and,
each site includes a portion adapted locally to deform in response to modest force applied from the reverse surface and to provide the site, when the board is in open configuration, for trans-panel insertion of a sponge via the reverse surface, and, as to a sponge in trans-panel insertion at a site and when force is no longer applied, to retain and display the sponge, with a part of said sponge protruding from the obverse surface and the board in open configuration, for tally.

7. A surgical sponge monitor board, to receive used surgical sponges for tally and subsequent disposal, which comprises
an hinge element with first and second aspects,
a first planar component on the hinge element at the first aspect,
a first base on the first planar component,
a second planar component on the hinge element at the second aspect, and
a second base on the second planar component,
whereof each planar component defines a plurality of sites; the hinge element enables the board to be turned to and between
(a) deployed configuration in which the planar components extend in upright stance on their respective bases, are coplanar and form a tally panel with a obverse surface and a reverse surface, and
(b) compact configuration in which the planar components are close to each other and approach parallelism, and the bases are outward; and,
each site includes a portion adapted locally to deform in response to modest force applied from the reverse surface and thereby to provide the site, with the board in deployed configuration, for trans-panel insertion of a sponge via the reverse surface, and, as to a sponge in trans-panel insertion at a site and when force is no longer applied, there to retain the sponge for tally, with a part of said sponge protruding from and displayed against the obverse surface, while the board is in deployed configuration, and for post-tally disposal with the board.

8. The monitor board of claim 7 where the planar components are rectangular and each component has inner, outer, upper and lower edge-portions; the hinge is intermediate the inner edge-portions; each panel defines slits at each deposit site; and, the deformable portion of a site comprises portions of the panel intermediate the slits of that site.

9. The monitor board of claim 8 where each planar component defines a small aperture at each deposit site of the component; the slits of a site are radial of the aperture; each base is trough comprising the lower edge-portion of a planar component, a lower web on said lower edge-portion, and a trough front on said lower web; the lower webs are generally coplanar; each planar component carries an upper channel comprising the upper edge-portion of the planar component, an upper web on said upper edge-portion and a fascia on said upper web; the upper webs are generally coplanar; each component carries a side channel comprising the outer edge-portion of the component; each fascia carries transparent and separable curtain elements for the reverse surface; and, when the board is in deployed configuration, said troughs and channels are together generally peripheral of the reverse surface, the board has a rectangular profile, the trough, fronts and fascia define a frontal plane, each side channel is within the plane, and the curtain elements are generally proximate the frontal plane; and, when the board is in compact configuration, said cases, channels and curtain elements are outward.

10. An assemblage comprising the monitor board of claim 9 and a container contoured to receive and encase the monitor board in compact configuration.

11. The assemblage of claim 9 where the monitor board comprises erectile construction, each planar component defines an upper slot and a lower slot, the trough front on each planar component carries a lower flap arranged to engage said component via and proximate the lower slot thereof, and the fascia on each planar component carries an upper flap arranged to engage said component via and proximate the upper slot thereof, thereby to provide and maintain erected status of the board.

12. Erectile construction according to claim 11 where each of the halves and each web, front and fascia are substantially planar and rectangular; each half defines an upper slot and a lower slot; each fascia has an upper flap to engage with the half on which the fascia is carried and via the upper slot defined by said half, each lower flap has a lower front to engage with the half on which the lower front is carried and via the lower slot defined by said half; transverse fold lines are parallel and perpendicular to the lateral fold lines; each site defines a trans-half aperture and slits extending from and radial of the aperture; the deformable portions of each site are intermediate the slits of the site; the blank is sheet material comprising 275 pound "C" board; and, the flaps for each said half, as engaged, serve to space the lower front and the fascia with reference to said half when the blank is in erected status.

13. A system for tally and disposal of surgical sponges including monitor board construction according to claim 9, a stand including a frame and a holder comprising upper and lower shelves on the frame and defining a rectangular channel corresponding to the rectangular profile of the construction in deployed configuration, so that the construction in deployed configuration may be carried on and subsequently demounted from the holder, and a disposal container for the construction when the construction has been demounted from the stand.

14. A system for tally and disposal of surgical sponges including the assemblage of claim 10, a stand including a frame and a holder comprising upper and lower shelves on the frame and defining a rectangular channel corresponding to the rectangular profile of the construction in deployed configuration so that the construction, when uncased from the container and in deployed configuration, may be carried on the shelves.

15. In an erectile monitor board construction formed from a blank of normally rigid and locally deformable sheet material a panel part
comprising a hinge element intermediate first and second halves,
defining first and second surfaces, inner and outer lateral fold lines, inner and outer transverse fold lines, at least one slot in each half, and a plurality of deposit sites whereof each site comprises small portions of the panel part which are locally deformable;

lower channel parts on each half, to comprise a trough, including a lower web extending from the half at a lower inner transverse fold line and a lower front extending from the lower web part at a lower outer transverse fold line;

upper channel parts on each half including an upper web extending from the half at an upper inner transverse fold line, and a fascia extending from the upper web at an upper outer transverse fold line; and, a least one flap for each half and on a channel part thereof, and adapted for engagement with said half via, respectively, a said slot thereof;

so that, when the halves are coplanar on the hinge element and the panel part has in-service orientation, deformable portions at a site adapt the site for insertion of a sponge from the first surface and to retain an inserted sponge with a portion thereof protruding from the second surface and visually displayed for tallying.

16. A monitor board, to receive surgical sponges for tally comprising a base with a lower web and a front on the lower web;
a tally panel
arranged to extend upwardly in in-service orientation from the base, and
defining an obverse surface, a reverse surface, a plurality of deposit sites, and a plurality of slits at each deposit site; and, an upper web extending from the panel, a fascia member on the upper web, and transparent and separable curtain elements for the first surface on the fascia member;

whereof each deposit site has a portion, intermediate the slits at the site, adapted locally to deform in response to modest force applied from the reverse surface and thereby to provide the site for trans-panel insertion of a sponge via the reverse surface and, as to a sponge in trans-panel insertion at the site and when force is no longer applied, there to retain the sponge protruding from and displayed against the background of the obverse surface.

* * * * *